United States Patent [19]

Sih

[11] 4,088,536

[45] May 9, 1978

[54] METHOD FOR PREPARING PROSTAGLANDINS

[75] Inventor: Charles J. Sih, Madison, Wis.

[73] Assignee: Wisconsin Alumni Research Foundation, Madison, Wis.

[21] Appl. No.: 772,019

[22] Filed: Feb. 25, 1977

Related U.S. Application Data

[62] Division of Ser. No. 221,058, Jan. 26, 1972, Pat. No. 4,031,129.

[51] Int. Cl.² .................................................. C12D 1/02
[52] U.S. Cl. ....................................................... 195/30
[58] Field of Search ........................................... 195/30

[56] References Cited

U.S. PATENT DOCUMENTS 3,840,434  10/1974  Daniels .................................... 195/30
3,968,141  7/1976  Sih et al. ............................. 195/30 X

*Primary Examiner*—Lionel M. Shapiro
*Attorney, Agent, or Firm*—Howard W. Bremer

[57] ABSTRACT

Racemic 15-deoxo, 11,15-deoxy and other prostaglandins and methods for preparing the same. The initial reactant is lithium cyclopentadiene which is reacted with ethyl-7-bromoheptanoate to give the alkylated diene which in turn is oxygenated to a mixture of hydroxycyclopentenones. 2-(6'-carboethoxyhexyl)-4-hydroxy-cyclopenten-1-one is chromatographically recovered from the mixture and reacted with dihydropyran to give the tetrahydropyranyl ether which is then reacted with 1-lithium-1-trans-octene in the presence of tri-n-butylphosphine-copper iodide to produce racemic 15-deoxy-prostaglandin $E_1$ ethyl ester which is chromatographically recovered. The ester is converted to the corresponding prostaglandin by the action of an esterase-producing microorganism.

1 Claim, No Drawings

METHOD FOR PREPARING PROSTAGLANDINS

The invention described herein was made in the course of work under a grant or award from the Department of Health, Education, and Welfare.

This is a division of application Ser. No. 221,058, filed Jan. 26, 1972, now U.S. Pat. No. 4,031,129, issued June 21, 1977.

This invention relates to prostaglandins and to intermediates used in the manufacture of prostaglandins and to methods for making such intermediates and prostaglandins.

The prostaglandins are cyclic, oxygenated $C_{20}$ fatty acids based on the prostanioc acid skeleton and elicit widespread physiological responses, for example, is the cardiovascular, nervous, reproductive renal and gastric systems of animals, including man, even at extremely low concentrations and amounts. Individual prostaglandins can manifest qualitatively different activities despite the commonality of the carbon skeleton of the various compounds. (For a comprehensive discussion of the prostaglandins, including nomenclature, methods of preparation, and physiologic activity see Annal of the New York Academy of Sciences, Vol. 180, Apr. 30, 1971 - a compilation of papers presented at a conference entitled Prostaglandins, held by the New York Academy of Sciences on Sept. 17-19, 1970.)

At the present time the supply of prostaglandins is limited. The total chemical syntheses heretofore suggested involve long and tedious steps and produce only minute quantities of the desired compounds. Derivation from natural sources is also not feasible because of the severe limitation, on the supply of such sources the consistency of their availability and the difficulties in extracting the desired compounds and obtaining them in significant amounts.

It is the principal purpose of this invention to overcome these problems by providing a process for preparing prostaglandins in good yield which is relatively simple and straightforward.

In addition, this invention provides new deoxyprostaglandins which exhibit prostaglandin-like activity or which can function as intermediates in the preparation of known prostaglandins. Such compounds have the general formula

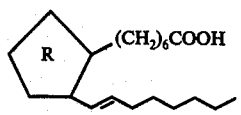

where

represents the basic ring structure of the F, E, A and B type prostaglandins or the

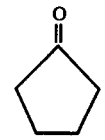

configuration.

Preparation of dl-15-deoxyprostaglandin $E_1$

EXAMPLE 1

The Roman numeral designations following specific compounds recited in this Example are identical with like designations in the schematic of the process set forth at the end of this Example.

A solution of $CH_3Li$(1.95 M, 0.65 mole, 333 ml.) was added under nitrogen to a magnetically stirred solution of freshly distilled cyclopentadiene (60 ml., 0.68 mole) in dry tetrahydrofuran (THF) (550 ml.) with ice bath cooling. To this resulting white suspension ethyl 7-bromoheptanoate (120 g., 0.54 mole) was added dropwise over a period of one-half hour. The mixture was allowed to warm to room temperature and stirred for 3 hours. The resulting clear solution was poured into water and extracted with ether (3 l). The extract was washed twice with water, one with saturated brine, dried ($MgSO_4$) and evaporated at room temperature. This process gave almost pure 2-carboethoxyhexyl-2-cyclopentene-1,4-diene (I).

The curde diene (I, 119 g., 0.54 mole) from the last reaction was dissolved in ethanol (6 l). This was cooled to $-10°$ C. and to this chilled solution 30% hydrogen peroxide was added (125 g., 1.1 mole). To this mixture a solution of potassium hypochlorite (840 ml., 1.15 mole, 1.37 N sol) was added dropwise over a period of 2 hours. After stirring at $-10°$ C. for an additional half hour, the reaction mixture was made acidic with 2 N HCl and ethanol was removed on a rotary evaporator. The residual oil was diluted with water and extracted with ether (3 l). The extract was washed with water, saturated brine solution, dried ($MgSO_4$) and stripped off the solvent to yield a yellow oil (120 g.).

The yellow oil (20 g.) was chromatographed over a silicic acid- Celite (85:15) column (1½ × 25 inches). The column was washed with two volumes of benzene-ethyl acetate (8.2). The desired 2-(6'carboxyethoxyhexyl-4-hydroxy-2-cyclopenten-1-one (1.5 g.) (II) was eluted from the column with 35% ethyl acetate in benzene while the positional isomer, 2-(6'-carboethoxyhexyl)-1-hydroxy-2-cyclopenten-4-one (5 g.) (III) was eluted from the column with 45% ethyl acetate in benzene.

Compound II (1 g.) was purified by rechromatography on another silicic acid-Celite (85:15) column (⅜ × 16 inches). The column was eluted with a gradient system consisting of 400 ml. of benzene-ethyl acetate (95:5) in the mixing chamber and 400 ml. of benzene-ethyl acetate (65:35) in the reservoir. 7 ml. fractions were collected. Fractions 53-94 were pooled and evaporated to dryness to yield 884 mg. of II which exhibited the following characteristics: $\lambda_{max}^{alc}$ 222 nm ($\epsilon$10,000), $\lambda_{max}^{Nujol}$ 2.90, 5.72 and 5.87$\mu$, nmr (CDCl$_3$) $\delta$1.21 ($t$, 3, J = 6.7 HZ, CH$_3$), $\delta$4.13 ($q$, 2, J = 6.7 HZ, CH$_3$CH$_2$), $\delta$4.93 ($m$, 1, H—C—OH), $\delta$7.23 ($m$, 1 vinyl H); molecular ion at m/e 254.

Similarly Compound III (1 g.) was repurified by chromatography over a silicic acid-Celite (85:15) column (⅜ × 15 inches). The column was eluted with gradient system consisting of 500 ml. of benzene-ethyl acetate (95:5) in the mixing chamber and 500 ml. of benzene-ethyl acetate (60:40) in the reservoir; 7 ml. fractions were collected. The desired compound, III, resided in fractions 134–149 which were pooled to yield 798 mg. of III which exhibited the following characteristics: $\lambda_{max}$ 224 nm ($\epsilon$13,500), nmr (CDCl$_3$) $\delta$1.22 ($t$, 3, J = 6.7 HZ, CH$_3$), $\delta$4.13 ($q$, 2, J = 6.7 HZ, CH$_3$CH$_2$), $\delta$4.88 ($m$, 1, J = 6 and 2.5 HZ, H—C—OH), $\delta$5.98 ($m$, 1, vinyl H), $\lambda_{max}^{Nujol}$ 2.92, 5.77 and 5.91$\mu$, molecular ion at m/e 254.

Preparation of the Tetrahydropyranyl ether (IV)

1 drop of concentrated hydrochloric acid was added to a mixture of 3.2 g. (13.3 mmoles) of the hydroxy ester (II) and 3.28 g. (~40 mmoles) of dihydropyran. The solution was shaken in order to effect mixing and was allowed to become warm and then allowed to stand at room temperature for 16 hours. The solution was rapidly diluted with ether. The resulting ether solution was washed successively with saturated sodium bicarbonate and saturated sodium chloride solutions and dried over magnesium sulfate. Evaporation of the ethereal solution yielded a yellow oil, wt: 4.557 g. which by shown by mnr analysis to be the required product. This oil was chromatographed on a silicic acid-Celite (85:15) column (1½ × 16 inches). The column was eluted with a gradient system consisting of 500 ml. of benzene in the mixing flask and 500 ml. of benzene-ethyl acetate (85:15) in the reservoir flask and 7 ml. fractions were collected. Fractions 68–120 were pooled and evaporated to dryness to give 2.7 g. of 2-(6'-carboethoxyhexyl)-2-cyclopentene-4-tetrahydropyranoxy-1-one (IV) which exhibited the following characteristics: $\lambda_{max}$222nm ($\epsilon$9,500), $\lambda_{max}^{Nujol}$ 5.73, 5.82 and 9.61$\mu$, nmr (COCl$_3$) molecular ion at 338.209310 theory for C$_{19}$H$_{30}$O$_5$, 338.212530).

A solution of tri-n-butylphosphine-copper (I) iodide complex (1.6127 g.) in 21 ml. of dry diethyl ether was treated with 34 ml. of 0.242 M solution of 1-lithium-1-trans-octene in ether at −78° C. under a blanket of nitrogen. After stirring at −78° C. for 30 minutes, 1.33 g. of the tetrahydropyranyl ether derivative (IV) in 25 ml. of dry diethyl ether was added dropwise to the yellow vinyl copper solution. The reaction was allowed to warm to 0° C. (ice-bath) and stirred at this temperature for 1.5-2 hours. The reaction mixture was allowed to warm to room temperature and 28 ml. of a 20% aqueous ammonium chloride solution, pH 8.3 was added to complex the copper. The ethereal layer was separated from the blue aqueous layer, which was extracted three times with ether. The combined ether extracts were washed twice with a saturated sodium chloride solution and dried over magnesium sulfate. Evaporation of the ethereal extract afforded a reddish yellow oil. This oil was dissolved in 10 ml. of acetic acid-water (65:35) and tetrahydrofuran in the ration of 1 to 0.1 ml. and was stirred at 30° C. overnight according to the procedure of E. J. Corey, T. K. Schaaf, W. Huber, U. Koelliber and N. Weinshenker, *J. Amer. Chem. Soc.*, 92, 397 (1970). The solvent was removed and the oily product was chromatographed over a silicic acid-Celite (85:15) column (¾ × 14 inches). The column was eluted with a gradient system consisting of 400 ml. of benzene in the mixing chamber and 400 ml. of benzene-ethyl acetate (75:25) in the reservoir. 7 ml. fractions were collected. Fractions 33-48 afforded 155 mg. of ultraviolet positive material which had the following characteristics: nmr (COCl$_3$) $\delta$1.21 ($t$, 3, J = 6.7 HZ, CH$_3$), $\delta$3.23 ($m$, 1, H at C-12), $\delta$4.13 ($q$, 2, J = 6.7 HZ, CH$_3$CH$_2$), $\delta$5.62 ($m$, 2, vinyl H at C-13 and C-14), $\delta$6.17 ($m$, 1, H at C-10), $\delta$7.49 ($m$, 1, H at C-11); m/e at 348; $\lambda_{max}^{alc}$ 217 nm ($\epsilon$10,000) and was identified thereby as dl 15-deoxy PGA$_1$ ethyl ester (IX).

Fractions 65-100 were pooled and evaporated to dryness to yield 717 mg. of a material having the following characteristics: nmr (CCl$_4$, 100 $m$ HZ) $\delta$1.21 ($t$, 3, J = 6.7 HZ, CH$_3$), $\delta$4.13 ($q$, 2, J = 6.7 HZ, CH$_3$CH$_2$), $\delta$4.20 ($m$, 1, H—C—OH), $\delta$5.28 ($d$ of $d$, J$_{12,13}$ = 7 HZ, J$_{13,14}$ = 16 HZ—C$_{13}$H=), 5.58 ($d$ of $t$, J$_{13,14}$ = 16 HZ, J$_{14,15}$ = 6 HZ, =C$_{14}$H—); ir (Nujol) 962 cm$^{-1}$ (trans CH=CH); molecular ion at m/e 366.28145 (theory for C$_{22}$H$_{38}$O$_4$, 366.27699) and which was determined to be dl-15-deoxoprostaglandin E$_1$ ethyl ester (VI).

The ester (VI) can be readily converted to dl-15-deoxy PGE$_1$ (VII) by methods which are well known in the art, such as, for example, by exposing it to the action of an esterase-producing microorganism. An example of the microorganism-induced conversion is set forth below.

EXAMPLE 2

To 15 g. of Red Star dry yeast, dissolved in 500 ml. of 0.1 M phosphate buffer, pH 7.0 was added 500 mg. of dl-15-deoxyprostaglandin E$_1$ ethyl ester (VI) in a two liter Erlenmeyer flask. The reaction mixture was incubated on a rotary shaker at 25° C. for 13 hours. The reaction mixture was then acidified to pH 2.5 with 5NHCl and extracted with three volumes of ethyl acetate three times. The combined ethyl acetate layer was dried over sodium sulfate and evaporated to dryness. The residue was chromatographed over a silicic acid-Celite (85:15) column (9/16 × 10 inches). The column was eluted with a gradient system consisting of 400 ml. of benzene-ethyl acetate (95:5) in the mixing flask and 400 ml. of benzene-ethyl acetate (1:1) in the reservoir flask; 7 ml. fractions were collected. Fractions 22-40 contained 202 mg. of recovered starting material, VI, whereas fractions 41-85 were pooled to yield 137 mg. of dl-15-deoxy prostaglandin E$_1$ (VII) [nmr (CDCl$_3$, 100 $m$ HZ) $\delta$4.08 ($q$, 1, H—C—OH), $\delta$5.29 ($d$ of $d$, J$_{12,13}$ = 6 HZ, J$_{13,14}$ = 15 HZ, —C$_{13}$H—), $\delta$5.69 ($d$ of $t$, J$_{13,14}$ = 15 HZ, J$_{14,15}$ = 6 HZ, =C$_{14}$H—); molecular ion at m/e 338.23891 (theory for C$_{20}$H$_{34}$O$_4$, 338.24569)].

Alternative to the procedure of Example 1, the mixture of hydroxycyclopentenones obtained from oxygenating the alkylated cyclopentadiene can be treated as follows in lieu of chromatographically separating the said mixture.

EXAMPLE 3

7 g. of the oily mixture of hydroxycyclopentenones was dissolved in 700 ml. of acetone and cooled in ice bath. To this solution was added 20 ml. of Jones reagent (chromic oxide and sulfuric acid in water) dropwise (1 ml. per minute) under stirring. After 30 minutes, 15 ml. of absolute methanol was added to destroy excess Jones reagent. The mixture was diluted with 500 ml. of water and evaporated to 700 ml. The aqueous layer was extracted with 250 ml. of ethyl ether three times. The combined ether layer was washed with K$_2$CO$_3$, dried over Na$_2$SO$_4$ and evaporated to dryness to yield 4 g. of an oily residue. The residue was chromatographed over a column (1½ × 16 inches) containing silicic acid-Celite (85:15). The column was eluted with a gradient consisting of 500 ml. of benzene-ethyl acetate (90:10) in the mixing chamber and 500 ml. of benzene-ethyl acetate (7:3) in the reservoir flask; 7 ml. fractions were collected. Fractions 128-141 contained a material having the following characteristics: m.p. 43°-45° C; nmr (CDCl$_3$) δ1.21 (t, 3, J = 6.7 HZ, CH$_3$), δ2.83 (S, 2, 10—CH$_2$), δ4.13 (q, 2, J = 6.7 HZ, CH$_3$CH$_2$) δ7.0 (t, 1, J = 1 and 1 and 1.5 HZ, Vinyl H); UV (methanol) λ$_{max}$232nm (ε12,800); m/e at 252 and which was identified as 2-(6'-carboethoxyhexyl)-2-cyclopentene-1,4-dione VIII.

This dione was then reduced as follows: A solution of 220 mg. (1 mmole) of freshly distilled aluminum isopropoxide (bp 130-140/7mm) in 10 ml. of anhydrous isopropyl alcohol (freshly distilled over CaH$_2$) was heated to reflux and 100 mg. (0.4 mmole) of the diketone (VIII) in dry isopropyl alcohol (1.5 ml.) was added by syringe over a period of 15 minutes. The isopropyl alcohol was distilled slowly through a short path distillation apparatus over a period of 2 hours keeping the volume in the reaction flask constant by addition of fresh isopropyl alcohol. The remaining alcohol was removed on a rotary evaporator. Ether (20 ml.) and water (5 ml.) were added and the mixture was acidified with 2 N HCl. The aqueous layer was extracted twice with ether. The combined ethereal layers were washed with water, dried and evaporated to afford a yellow gum (110 mg.).

The gum was dissolved in a benzene-ethyl acetate mixture (8:2 volume ratio) and chromatographed over a silicic acid-Celite (85:15) column (1½ × 25 inches). The column was washed with two volumes of benzene-ethyl acetate (8:2) and the desired 2-(6'carboethoxyhexyl)-4-hydroxy-2-cyclopenten-1-one (II) as the isopropyl ester was eluted from the column with 35% ethyl acetate in benzene.

Following elution and recovery of the isopropyl ester of compound II, the procedure of Example 1 was followed in subsequent steps beginning with the preparation of the tetrahydropropanyl ether (IV) through the recovery of dl-deoxyprostaglandin E$_1$.

Following is a single schematic diagram including the processes as described in the foregoing Examples.

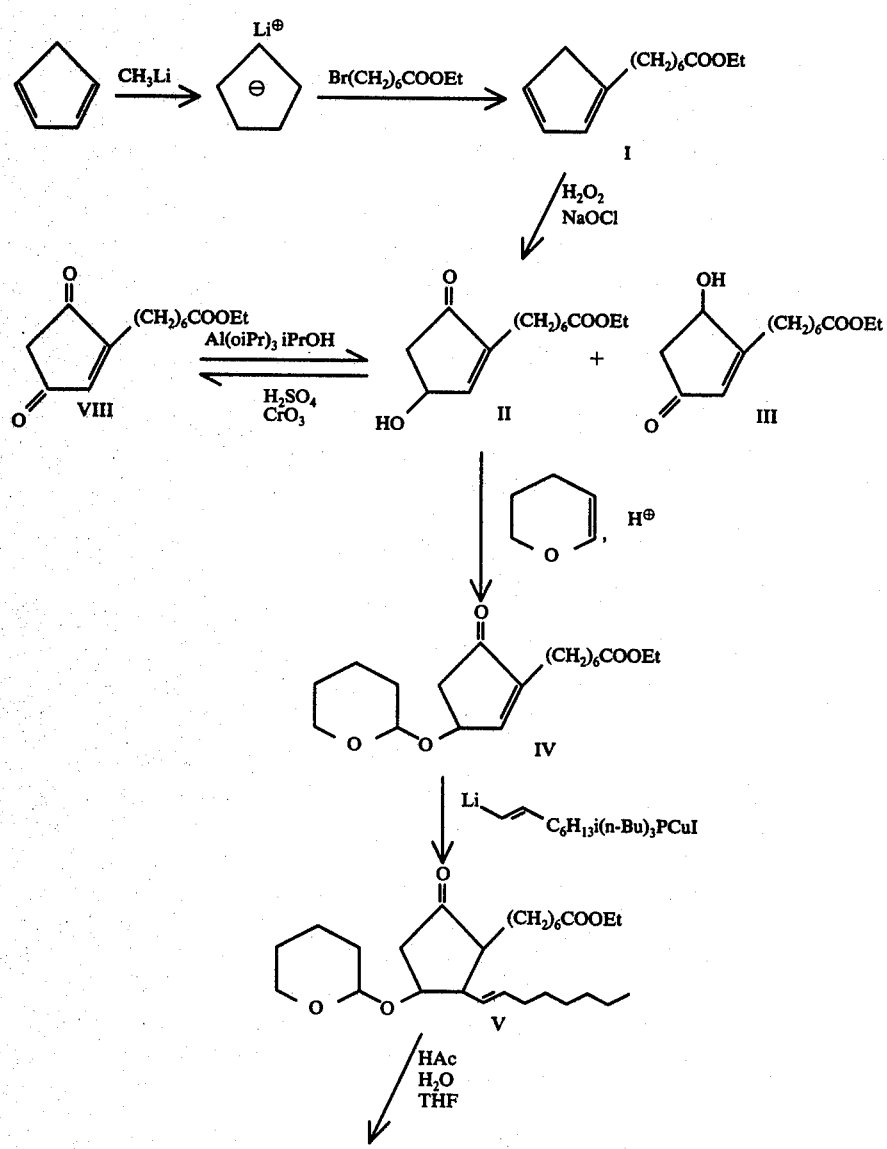

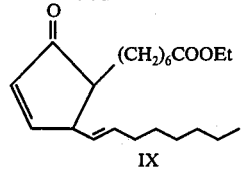

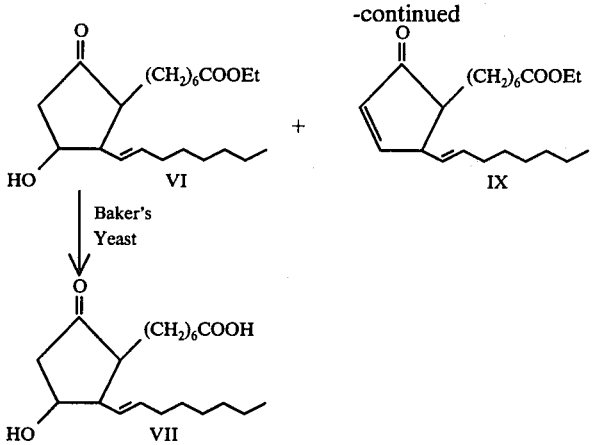

In the preceeding Examples the 1-lithium-1-trans-octene reactant was made as follows: In a three-necked round bottom flask equipped with a mechanical stirrer (wire blade) and pressure equalizing dropping funnel was placed 4-6 molar equivalents of fine lithium powder and dry diethyl ether (2 ml/1 mmole of vinyl iodide) freshly distilled over lithium aluminum hydride. A blanket of argon was maintained at all times. To this rapidly stirred mixture, which was cooled in an ice-bath, was added 1 molar equivalent of 1-iodo-1-trans-octene (vinyl iodide) in dry diethylether (2 ml/1 mmole of vinyl iodide). After a few drops of the vinyl iodide in ether was added, a Gilman test was performed. If the test was positive, the addition of the vinyl iodide was continued. If the test was negative, the addition of the vinyl iodide was stopped and the rapid stirring of the lithium solution continued. The Gilman test was performed at various intervals. When a positive test was obtained, the addition of the vinyl iodide was recommenced. The vinyl iodide solution was added over 2 hours. The solution was stirred with ice-bath cooling for a further 4 hours. The solution of the vinyl lithium was transferred to a storage bottle under argon through a glass wool filter (to filter out any unreacted lithium). Before use the vinyl lithium was titrated with an HCl solution to determine concentrate of the vinyl lithium solution.

The vinyl iodide reactant in the above described process for making vinyl lithium was prepared in accordance with the general procedure described by G. Zweifel et al, J. Amer. Chem. Soc. 89, 2753 (1967) and as described below.

2 molar equivalents of diisobutylaluminum hydride were added to 1 molar equivalent of 1-octyn-3-ol in dry heptane (40 ml/100 m moles of 1-octyn-3-ol) while maintaining the temperature below 40° C. When the exothermic reaction had subsided, the reaction mixture was heated at ca 50° C. for 2.5 hours. The heptane was then removed under reduced pressure (0.2 mm Hg) and the residue obtained was diluted with dry tetrahydrofuran (40 ml/100 m moles of diisobutylaluminum hydride). To this solution cooled to −50° was slowly added a solution of 2 molar equivalents of iodine in dry tetrahydrofuran (40 ml/100 m moles of iodine) while maintaining the temperature at about −50° C. The iodine colour disappeared at the beginning and a gas, probably hydrogen, was given off. After about 1 molar equivalent of iodine was added, the gas evolution ceased and the iodine colour disappeared more slowly, the solution taking on a red colour. After all the iodine had been added, the reaction mixture was allowed to warm up to room temperature, whereupon the diisobutylalane was decomposed at 20°-30° C. by the dropwise addition of 20% sulfuric acid. When the isobutane evolution had diminished, the reaction mixture was poured into ice - 20% sulfuric acid. The reaction mixture was extracted four times with pentane and the combined organic extract was washed successively with sodium thiosulfate, saturated sodium bicarbonate and saturated sodium chloride solutions, and dried over magnesium sulfate. Evaporation of the dried extract gave a yellow oil. The nmr spectrum (CDCl$_3$) of the product after all volatile material had been distilled off, showed that some of the saturated iodide, 3-hydroxy-1-iodo-octane was present.

The product was further treated to remove any 3-hydroxy-1-iodo-octane and possible diiodo-3-hydroxyoctane present. To accomplish this the reaction product was mixed with an excess (3-5 times) of triethylamine and the mixture heated at ca 94° for 20 hours. The excess triethylamine was evaporated off and water was added to the residue. The mixture was shaken for some time. Most of the black oily residue dissolved in the water and the total mixture was extracted five times with pentane. The combined pentane extract was washed successively with dilute hydrochloric acid, saturated sodium bicarbonate, sodium thiosulfate, saturated sodium bicarbonate and saturated sodium chloride solutions and dried over magnesium sulfate. The product obtained after evaporation of the pentane was chromatographed on silica gel and elution with benzene produced pure 3-hydroxy-1-iodo-1-trans-octene, wt: 12.5 g. (24.6%).

It will be evident to those skilled in the art that dl-15-deoxyprostaglandin E$_1$, can be functionalized at the C-15 position to yield prostaglandin E$_1$ using standard methods of allylic oxidation such as, selenium dioxide oxidation, n-bromo-succinimide and silver acetate or n-bromo-succincimide and lead tetraacetate (see Fieser and Fieser, Reagents for Organic Synthesis, John Wiley & Sons, Inc., 1967).

Also the dl-15-deoxy PGA$_1$ and PGB$_1$ series can be obtained by well known means, i.e. by treating dl-15-deoxo PGE$_1$ with an acid or base to convert it to the PGA$_1$ series and then treating the PGA$_1$ series with a base to convert it into the PGB$_1$ series.

In addition, the 9keto function in dl-15-deoxyprostaglandin E$_1$ can readily be reduced by metal hydrides, such as sodium borohydride to yield an alcoholic function at the 9-position, giving rise to the PGF$_1$ series of prostaglandins. Alternatively, the $PGF_1$ series can be obtained by incubating dl-15-deoxyprostaglandin $E_1$ with baker's yeast as described in Example 2 but allowing the microorganism-induced conversion to proceed for a longer period of time without termination.

In the aforedescribed procedure (Example 1) vinyl lithium is reacted with a soluble form of copper to produce vinyl copper for reaction with the tetrahydropyranyl derivative. Forms of soluble copper other than tri-n-butylphosphine copper-iodide complex may be utilized for the production of the vinyl copper. For example, $(n-Bu_2S)_2$ Cu I is also suitable for such reaction.

Pharmacological assays were conducted with dl-15-deoxyprostaglandin $E_1$ using the guinea pig tracheal strip (smooth muscle) methods described by J. W. Constantine, Journal Pharmacy & Pharmacology 17, 3184 (1955) and R. Patterson, Journ. Allergy 29, 165 (1958). dl-15-deoxyprostaglandin $E_1$ exhibited an $ED_{50}$ concentration (effective dose giving 50% of maximum response) on separate determinations of $1.4 \times 10^{-6}M$ and $1.06 \times 10^{-6}M$ indicating its pharmacological applicability in place of natural prostaglandins where smooth muscle controlling or responsive effects are being sought.

Preparation of Prostaglandin $E_1$ Ethyl Ester

In the following Example the reactant 3-(α-ethoxy)-ethoxy-1-iodo-trans-1-octene was prepared as follows:

One drop of concentrated hydrochloric acid was added to a mixture of 1.53 g. (6 mmoles) of 3-hydroxy-1-iodo-trans-1-octene and 0.864 g. (12 mmoles) of ethyl vinyl ether. The solution was mixed and allowed to become warm and allowed to atand at room temperature for 4 hours. The solution was rapidly diluted with diethyl ether. The resulting solution was washed with a saturated sodium bicarbonate solution and a saturated sodium chloride solution and dried over magnesium sulfate. Evaporation of the ethereal solution yielded a yellow oil which was identified as 3-(α-ethoxy)-ethoxy-1-iodo-trans-1-octene.

EXAMPLE 4

Into a 25 ml. three-neck round bottom flask equipped with a mechanical stirrer (wire blade) and pressure equalizing dropping funnel was placed 160 mg. (23 mmoles) fine lithium powder and 10 ml. dry diethyl ether (freshly distilled over lithium aluminum hydride). A blanket of argon was maintained at all times. To this rapidly stirred mixture which was cooled in an ice-bath was slowly added a solution of 652 mg. (2 mmoles) 3-(α-ethoxy)-ethoxy-1-iodo-trans-1-octene in 8 ml. dry diethyl ether over a period of 2 hours. (After about 0.5 ml. of this solution had been added a positive Michler's ketone test was obtained). The reaction mixture was rapidly stirred for a further 3 hours.

The resulting vinyl lithium solution cooled to $-10°$ C. - $-15°$ C. (ice-salt bath) was siphoned through a glass wool filter into a solution of 196 mg. (0.5 mmoles) of copper iodide-tri-n-butylphosphine complex in 5 ml. of dry diethyl ether cooled to $-78°$ C. The resulting solution was stirred for 1 to 4 hours.

To this solution was added 170 mg. (0.5 mmoles) of 2-(6'-carboethoxyhexyl)-2-cyclopentene-4-tetrahydropyranoxy-1-one IV the preparation of which was accomplished as set forth in Example 1. This solution was allowed to warm to $-15°$ C. (ice-salt bath) and stirred as the solution warmed from $-15°$ C. to $0°$ C. over an hour. The solution was stirred at $0°$ (ice bath) for a further 2 hours and was then allowed to warm to room temperature. 15 ml. of a 20% aqueous ammonium chloride-ammonia solution of pH 8.1 was added and the resulting solution stirred. The upper ether solution was separated from the blue aqueous solution which was extracted a further four times with ether. The combined ether extract was washed with a saturated sodium chloride solution and dried over magnesium sulfate. Evaporation of the ether solution gave a dark red solution.

To remove the protecting tetrahydropyranyl and ethoxy-ethoxy ether groups from the product a mixture of the above crude product, 13 ml. of tetrahydrofuran was stirred at 37° C. for 6 hours. The solvent was removed under reduced pressure and the product chromatographed on a silicic acid-Celite (85:15) column (¾ × 12 inches). The column was eluted with 500 ml. of benzene-ethyl acetate (9:1) in the mixing flask and 500 ml. of benzene-ethyl acetate (1:1) in the reservoir; 6 ml. fractions are collected. Fractions 97-110 were concentrated to dryness to yield 14 mg. of a material having the following characteristics: nmr ($CDCl_3$) δ0.87 ($t$, 3, $CH_3$ at C-20), δ1.21 ($t$, 3, J = 6.7 HZ, $CH_3$), δ4.13 ($q$, 2, J = 6.7 HZ, $CH_3CH_2$), δ4.08 ($m$, 2 protons at C-11 and C-15), δ5.65 ($m$, 2, vinylic protons at C-13 and C-14), m/e at 382 (M+) and which was identified thereby as 11,15-diepi $PGE_1$ ethyl ester. Fractions 111-136 were combined to yield 43 mg. of a material whose nmr spectrum were similar but the splitting pattern of the vinylic protons of which were different than 11,15-diepi-$PGE_1$-ethyl ester and which, on thin layer chromatography (TLC), developed in ethyl acetate-acetic acid-isooctane-water (110:20:50:100) was slightly more polar than 11,15-diepi-$PGE_1$ ethyl ester but slightly less polar than $PGE_1$ ethyl ester. This material was identified as 15-epi-$PGE_1$-ethyl ester. Fractions 157-240 were pooled to give 53 mg. of $PGE_1$ ethyl ester, whose nmr, mass spectrum and infrared spectrum were identical to a known specimen of that material. Also, TLC developed in the aforementioned solvent system showed it had the same mobility as the known specimen $PGE_1$ ethyl ester.

The $PGE_1$ ethyl ester can be readily converted to $PGE_1$ by methods well known in the art such as by exposure to the action of an esterase-producing microorganism such as baker's yeast. Such conversion applied to dl-15-deoxyprostaglandin $E_1$ ethyl ester is shown in Example 2 supra.

Following is a simplified schematic of the process of this Example 4 beginning with the reaction between the tetrahydropyranyl ether and the vinyl lithium.

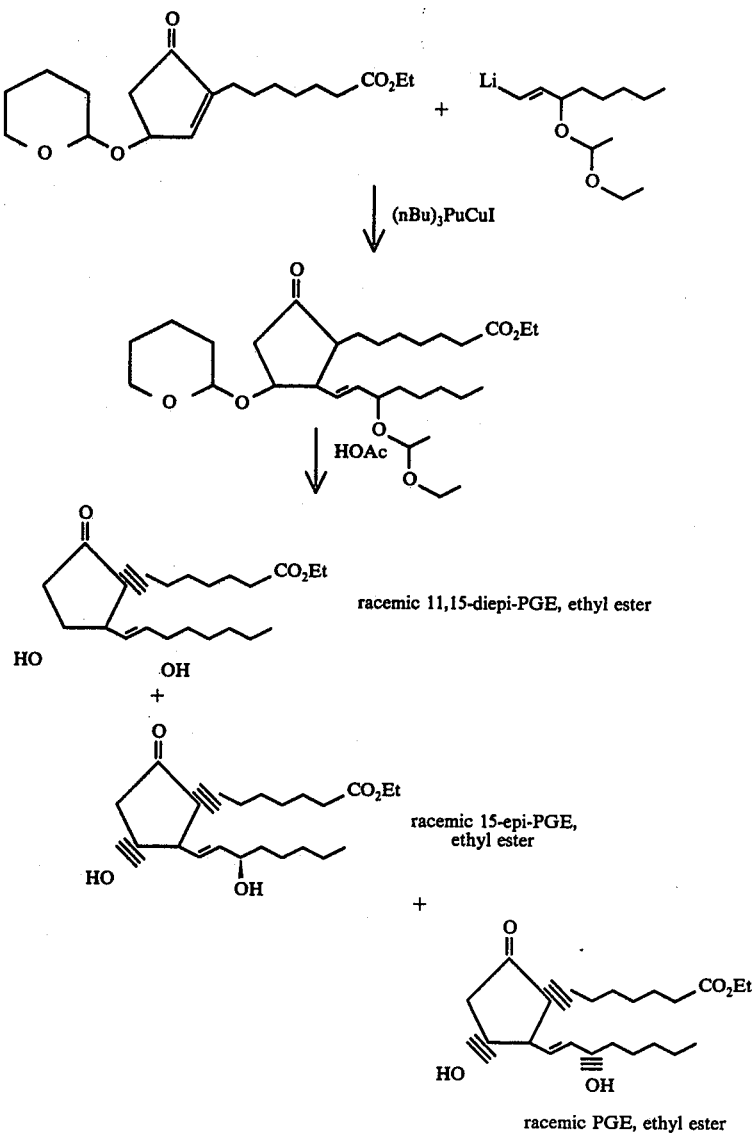

EXAMPLE 5

Preparation of dl-11-Deoxyprostaglandin $E_1$ Methyl Ester 3-(α-ethoxy)-ethoxy-1-lithium-1-trans-octene was prepared as described supra.

326 mg. (1 mmole) of 3-(α-ethoxy)-ethoxy-1-iodo-1-trans-1-octene in 4 ml. of ether was treated with 80 mg. of lithium powder in 5 ml. ether at 0°.

The resulting vinyl lithium ether solution was siphoned through a glass wool filter into 125 mg. (0.32 mmoles) of tri-n-butylphosphine-copper (I) iodide complex in 2 ml. dry diethyl ether at −78° C. (dry iceacetone). This solution was stirred at −78° C. 20 minutes, whereupon 107 mg. (0.31 mmoles) of 2-(6-carbomethoxyhexyl)-2-cyclopenten-1-one in 2 ml. of ether was added. The reaction solution was allowed to warm to −10° C. and stirred at −10°-0° C. for 1 hours. Stirring was continued at 0° C. for a further hour. 3 ml. of 20% aqueous $NH_4Cl/NH_3$ solution of pH 8.1 was added and the solution stirred until 2 clear layers were formed. The upper yellow organic layer was separated from the blue aqueous layer, which was extracted a further 3 times with ether. The combined ether extract was washed with a saturated sodium chloride solution and dried. Evaporation gave a dark red oil.

The oil (280 mg.) was chromatographed over a silicic acid-Celite (85:15) column (¾ × 12 inches). The column was eluted with 400 ml. of benzene in the mixing chamber and 400 ml. of benzene-ethyl acetate (8:2) in the reservoir chamber. 6 ml. fractions were collected. Fractions 92-134 (53 mg.) were combined and treated with hydrochloric acid to remove the protecting group to yield, upon rechromatography, 30 mg. of a material having the following characteristics: molecular ion at 352 (M+); 281 (M-71), nmr δ3.65 (3H, S, $CH_3$), 4.0 (1H, m, carbinolic proton at C-15); 5.62 (2H, m, vinylic protons at C-13 and C-14) and which was identified as dl-11-deoxyprostaglandin $E_1$ methyl ester.

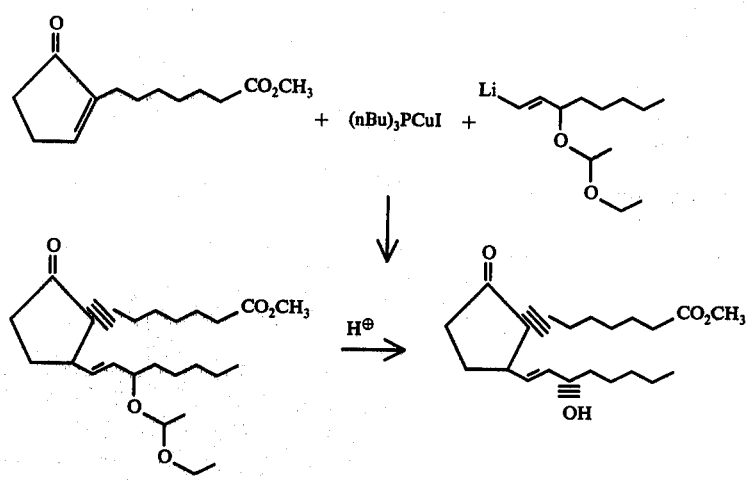

EXAMPLE 6

Preparation of dl-11,15-Dideoxyprostaglandin $E_1$

A solution of copper (I) iodide-tri-n-butylphosphine complex (1.175 g., 3.0 mmoles) in dry diethyl ether (2.5 ml.) was treated with a solution of trans-1-lithio-1-octene (22.5 ml., 6.08 mmoles, 0.27M; prepared in accordance with the procedure set forth hereinbefore and in the Zweifel article, supra.) in ether (added dropwise via syringe) at −78° C. under a blanket of nitrogen. After stirring at −78° C. for 30 minutes, 2-(6'-carbomethoxyhexyl)-2-cyclopenten-1-one (450 mg., 2 mmoles) was added dropwise via syringe and the solution warmed to 0° C. and stirred for an additional 2 hours at 0° C. (ice bath). Finally the mixture was allowed to warm to room temperature, whereupon the yellow solution began darkening after about 30 minutes. 20 ml. of 20% $NH_4Cl$ (aqueous) saturated with $NH_3$ were added until pH 9 was reached. The resulting mixture was filtered with suction. The residue was washed well with ether (50 ml.) and the combined filtrate and washings were shaken in a separatory funnel. The phases were separated and the aqueous phase was further extracted with ether (2 × 50 ml.). The combined ethereal extract was washed with a saturated aqueous sodium chloride solution (50 ml.) and dried ($MgSO_4$). After evaporation of the ether, the crude oily residue was chromatographed on 150 g. silica gel using a chloroform-benzene gradient starting with pure benzene and 2 liters of chloroform were used. After this elution was continued with pure chloroform. Approximately 500 mg. of the crude dl-11,15-dideoxyprostaglandin $E_1$ methyl ester was treated with 400 mg. (10 mmoles) of NaOH in 5 ml. of water and 15 ml. of methanol. The mixture was stirred magnetically for 15 hours and the methanol was then removed by evaporation. The aqueous phase was diluted with 5 ml. of water and the resulting mixture was extracted with ether. The aqueous phase was then acidified with hydrochloric acid and extracted with ether. The combined ether layers were dried over magnesium sulfate and the solvent was removed to yield 255 mg. of a material having the following characteristics: molecular ion at m/e 322.25058 (theory 322.25078 for $C_{20}H_{34}O_3$); nmr δ5.5 (2H, m, vinylic protons at C-13 and C-14) and which was identified as dl-11,15-dideoxyprostaglandin $E_1$.

The dl-11,15-dideoxy $PGE_1$ can be readily converted by known procedures (see above on conversion of dl-15-deoxy $PGE_1$) to dl-11-deoxy $PGE_1$ which can, via bromination and debromination (also known procedures), be converted to $PGA_1$ and which can in turn be converted by known procedures to $PGB_1$, $PGE_1$, and $PGF_1$.

For the synthesis of optically-active $PGE_1$ and 11-deoxy $PGE_1$ as described hereinbefore, optically active octyn-3-ol ($[\alpha]_D^{25}$ −23°) can be used to prepare the reactant 3 hydroxy-1-lithio-1-trans-octene ($[\alpha]_D^{25}$ −46°).

Preparation of 2-(6'-carbomethoxyhexyl)-2-cyclopenten-1-one

The reactant, 2-(6'-carbomethoxyhexyl)-2-cyclopenten-1one, in the preceding Examples was prepared as set out in the following Example wherein the Roman numerals identifying certain compounds identify the same compounds in the schematic diagram immediately following this Example.

EXAMPLE 7

Into a dry 3-necked flask equipped with a septum stopper, thermometer well adapter, pressure equilizing dropping funnel, and magnetic stirrer was placed dry tetrahydrofuran (200 ml/1 mole of octadiene) and 6.45 molar equivalents of octadiene (freshly distilled over calcium hydride). A blanket of nitrogen was maintained at all times. The flask was placed in a water bath at 25° C. Conversion to the trialkylborane was achieved by the dropwise addition of a solution of diborane in tetrahydrofuran (1 molar equivalent of hydride). The temperature of the solution was maintained at 25° C. by the addition of ice to the water bath. The solution was stirred at 25° C. for 1 hour, then methanol (13 ml/1 mole of hydride) was added to destroy excess hydride. 0.28 molar equivalents of iodine were added all at once, followed by 0.28 molar equivalents of 3M solution of sodium hydroxide in methanol over a period of 5 minutes. The reaction mixture was allowed to warm up and stirred for a further 15–20 minutes. The reaction mixture was poured into water containing sodium thiosulfate (1g/50 ml. of water) to remove excess iodine, and the aqueous layer was extracted three times with pentane. The combined pentane extract was dried over magnesium sulfate. The pentane and most of the excess octadiene was removed by rotary evaporator and the remaining material was distilled over calcium hydride under reduced pressure to give 8-iodo-1-octene.

0.086 mole of the 8-iodo-1-octene in 50 ml. of tetrahydrofuran was added dropwise to a mixture of 2.5 g. of Mg turnings in 20 ml. of dry tetrahydrofuran with mechanical stirring (under a blanket of nitrogen). After completion of the addition (~1 hr.), the mixture was boiled under gentle reflux for an additional 30 minutes. To this cooled Grignard reagent was added dropwise 0.085 mole of 2-methoxy-2-cyclopentene-1-one followed by stirring at room temperature for 30 minutes. The resulting mixture was poured onto 200 g. of chipped ice and 30 g. of NH$_4$Cl. One hundred ml. of 2 N HCl was then added. After shaking for 30 minutes the product was extracted with several portions of Et$_2$O (500 ml. total). The combined extracts were washed with two 50 ml. portions of saturated NaHCO$_3$, then with 100 ml. of saturated NaCl, and dried over Na$_2$SO$_4$. After evaporation of solvent approximately 14 g. of the crude product (I) was obtained.

Dehydration

To 9.4 g. of I, dissolved in 70 ml. of anhydrous methanol was added 2 ml. of concentrated H$_2$SO$_4$ and the mixture was refluxed for 14 hours. The cooled mixture was neutralized by the addition of solid NaHCO$_3$. After removal of the methanol, 200 ml. of water was added and the resulting mixture was exhaustively extracted with Et$_2$O (total of 600 ml.). The combined extracts were washed with 150 ml. of saturated aqueous NaCl and dried over MgSO$_4$. After filtration, the solvent was removed by rotary evaporation and the residual oil was distilled under reduced pressure. The fraction boiling 87°–89° (0.2 mm.) was collected as pure 2-(1'-octene-8-yl)-2-cyclopentene-1-one (II) (4.3 g., 40–50% yield.

Epoxidation of II 1.77 g. of the olefin (II) was dissolved in 8 ml. of methylene chloride was treated dropwise with a solution of m-chloroperbenzoic acid (1.7 g.) in 20 ml. of methylene chloride. The mixture was allowed to stand at 0° C. for two days. After the usual work up, the crude mixture was chromatographed over a silicic acid-Celite (85:15) column. The column was eluted with a gradient system comprising benzene and benzene-ethyl acetate (1:1). The pure epoxide obtained was 0.89 g. and the unreacted substrate was 0.96 g. which can be recycled.

Periodic acid cleavage of the epoxide (III)

The epoxide III (200 mg.) was dissolved in 10 ml. of ether. This was treated with a freshly prepared solution of periodic acid (assuming 9 mg/ml; 24 ml. of this solution (2 moles)). The mixture was then diluted with water and the organic layer was separated, washed with water, dried over sodium sulfate and evaporated to dryness to yield the desired aldehyde (IV).

Oxidation of the aldehyde to acid (V)

The aldehyde (IV) (200 mg.) was dissolved in ethyl ether (1 ml.) and added dropwise to a suspension of Ag$_2$O at 0° C. The mixture was stirred for 1 hour; the silver oxide at this point turned black. The black precipitate was filtered off and the filtrate was extracted with methylene chloride three times to remove unreacted aldehyde (39 mg.). The aqueous layer was made acidic to pH 2 and exhaustively extracted with ethyl acetate. The combined ethyl acetate layers were dried over sodium sulfate and evaporated to yield 139 mg. of pure acid.

Esterification of the acid (V) was achieved by treating the acid with diazomethane in accordance with known methods to yield 2-(6'-carbomethoxyhexyl)-2-cyclopenten-1-one (VI). This compound, as is evident from the foregoing discussion and Examples is a basic reactant in the preparation of dl-11 and dl-11,15-deoxyprostaglandins.

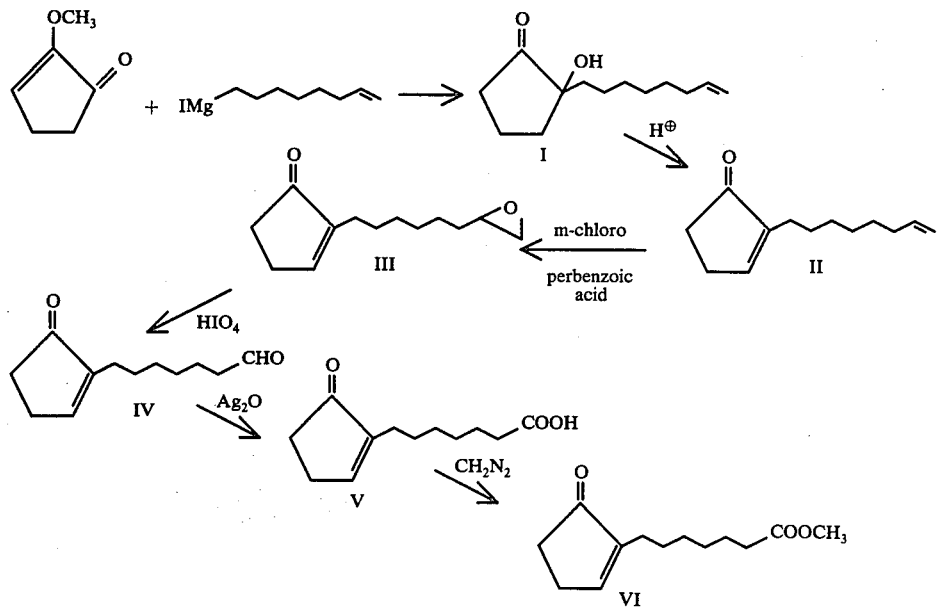

In the foregoing Examples the conversion of the dl 11-deoxy PGE$_1$ esters to, respectively, dl-11-deoxo PGE$_1$ and dl-15-deoxy PGE$_1$ can be readily accomplished by mold organism such as, for example, aspergillus and penicillum. Also, the proportions and amounts of reactants is not critical although it is obvious that changes in proportions and amounts will have an effect on the yields of desired products obtained from the various reactions.

What is claimed is:

1. A method for preparing PGE$_1$ which comprises:

alkylating lithium cyclopentadiene with ethyl-7-bromo-heptanoate oxygenating the resulting alkylated cyclopentadiene to produce a mixture of hydroxycyclopentenones chromatographically separating the said mixture and recovering 2-(6'-carboethoxyhexyl)-4-hydroxy-cyclopenten-1-one reacting the said recovered hydroxy ester with an excess of dihydropyran in the presence of an acid catalyst and recovering 2-(6'-carboethoxyhexyl)-2-cyclopentene-4-tetrahydropyranoxy-1-one from the reaction mixture reacting the said ether with the oxygenated vinyl lithium derivative obtained from the reaction of lithium powder and 3-($\alpha$-ethoxy)-ethoxy-1-iodo-trans-1-octene in the presence of tri-n-butylphosphine-copper iodide complex and recovering the formed prostanoic acid derivative from the reaction mixture removing the tetrahydropyranyl and ethoxy-ethoxy ether groups from the said derivative chromatographically recovering $PGE_1$ ethyl ester from the reaction mixture and exposing the said ester to the action of an esterase-producing microorganism and recovering $PGE_1$ from the reaction mixture.